US006729195B2

(12) United States Patent
Graze, Jr.

(10) Patent No.: US 6,729,195 B2
(45) Date of Patent: May 4, 2004

(54) SERIAL MULTISTAGE AEROSOL DILUTER AND CONTROL SYSTEM

(75) Inventor: Russell R. Graze, Jr., Dunlap, IL (US)

(73) Assignee: Caterpillar Inc, Peoria, IL (US)

( * ) Notice: Subject to any disclaimer, the term of this patent is extended or adjusted under 35 U.S.C. 154(b) by 275 days.

(21) Appl. No.: 09/852,815

(22) Filed: May 10, 2001

(65) Prior Publication Data

US 2002/0166390 A1 Nov. 14, 2002

(51) Int. Cl.[7] .................................................. G01N 1/00
(52) U.S. Cl. .................................. 73/863.03; 73/864.73
(58) Field of Search .......................... 73/863.01, 863.02, 73/863.03, 864.73, 864.74, 23.31, 23.32, 1.16, 1.06

(56) References Cited

U.S. PATENT DOCUMENTS

| | | | |
|---|---|---|---|
| 3,699,814 A | | 10/1972 | Kaufman |
| 3,846,075 A | | 11/1974 | Cioffi |
| 4,445,359 A | | 5/1984 | Smith |
| 4,670,135 A | | 6/1987 | Marple et al. |
| 5,058,440 A | * | 10/1991 | Graze, Jr. |
| 5,493,891 A | | 2/1996 | Slemeyer |
| 5,509,292 A | * | 4/1996 | D'Appollonia et al. |
| 5,587,519 A | | 12/1996 | Ronge et al. |
| 5,614,655 A | | 3/1997 | Horn |
| 5,703,299 A | | 12/1997 | Carleton et al. |

* cited by examiner

*Primary Examiner*—Robert Raevis
(74) *Attorney, Agent, or Firm*—Larry G Cain

(57) ABSTRACT

An exhaust gas sampling system for use in connection with the sampling of an internal combustion engine exhaust gas streams has a plurality of diluters arranged in a serial array along an axial extent. A source of engine exhaust gas is fluidically connected to the plurality of serially arranged diluters so as to supply an engine exhaust gas stream into each one of the plurality of serially arranged diluters in a serial manner. A source of dilution air fluidically is connected to each one of the plurality of serially arranged diluters so as to supply dilution air into each one of the plurality of serially arranged diluters. The dilution air is supplied into the engine exhaust gas stream present within each one of the plurality of serially arranged diluters so as to progressively dilute the engine exhaust gas stream as the engine exhaust gas stream flows through the plurality of serially arranged diluters and thereby replicate engine exhaust gas stream pollutant atmospheric conditions, and sampling apparatus fluidically connected to each one of the plurality of serially arranged diluters for obtaining and analyzing a sample of diluted engine exhaust gas stream present within each one of the plurality of serially arranged diluters.

18 Claims, 4 Drawing Sheets

SERIAL MULTISTAGE AEROSOL DILUTER AND CONTROL SYSTEM

DESCRIPTION

1. Technical Field

The present invention relates generally to measurement systems for accurately measuring the amount of particulate pollutants within the exhaust gas stream of an engine, and more particularly to a measurement system which not only accurately measures the amount of particulate pollutants within the exhaust gas stream of an engine but which can also replicate engine exhaust stream characteristics under highway or roadway atmospheric conditions so as to additionally determine the size of the particulates which are prevalent within real atmospheric conditions.

2. Background Art

Exhaust emissions from motorized highway vehicles are currently regulated by the Federal Government and therefore must not exceed predetermined contaminant levels as set forth, for example, within Title 40, Chapter 1 of the Code of Federal Regulations, Section 86, Subpart C. As a result of these regulations, increasingly more sophisticated testing equipment has been developed to test and analyze engines for conformance with such standards. For example, one regulation established by the Environmental Protection Agency (EPA) sets a particulate limit standard of 0.60 g/hph for diesel truck engines wherein the particulates are defined as matter. Such matter being agglomerated carbon particles absorbed hydrocarbons, and sulphates. Condensed water which is not considered matter can be collected on a special filter after dilution of the exhaust gas stream by ambient air to a maximum temperature level of 52 degrees C. or 125 degrees F.

In order to obtain consistent or reliable results, it is mandatory that the fluidic addition of the dilution air be accomplished at accurately controlled flow rates which may nevertheless be varied within predetermined ranges depending upon the operating temperature and pressure levels or parameters. A system for achieving such a goal has in fact been previously developed by the present inventor and is disclosed within U.S. Pat. No. 5,058,440 which issued on Oct. 22, 1991.

The present invention is directed to overcoming one or more of the problems as set forth above.

DISCLOSURE OF THE INVENTION

In one aspect of the invention a sampling system has a plurality of diluters arranged in a serial array along an axial extent; a source of gas fluidically connected to the plurality of serially arranged diluters so as to supply a gas stream into each one of the plurality of serially arranged diluters in a serial manner; a source of dilution air fluidically connected to each one of the plurality of serially arranged diluters so as to supply dilution air into each one of the plurality of serially arranged diluters such that the dilution air is supplied into the gas stream present within each one of the plurality of serially arranged diluters so as to progressively dilute the gas stream as the gas stream flows through the plurality of serially arranged diluters; and sampling apparatus fluidically connected to each one of the plurality of serially arranged diluters for obtaining the analyzing a sample of the diluted gas stream present within each one of the plurality of serially arranged diluters.

BEST MODE FOR CARRYING OUT THE INVENTION

Figure 1:
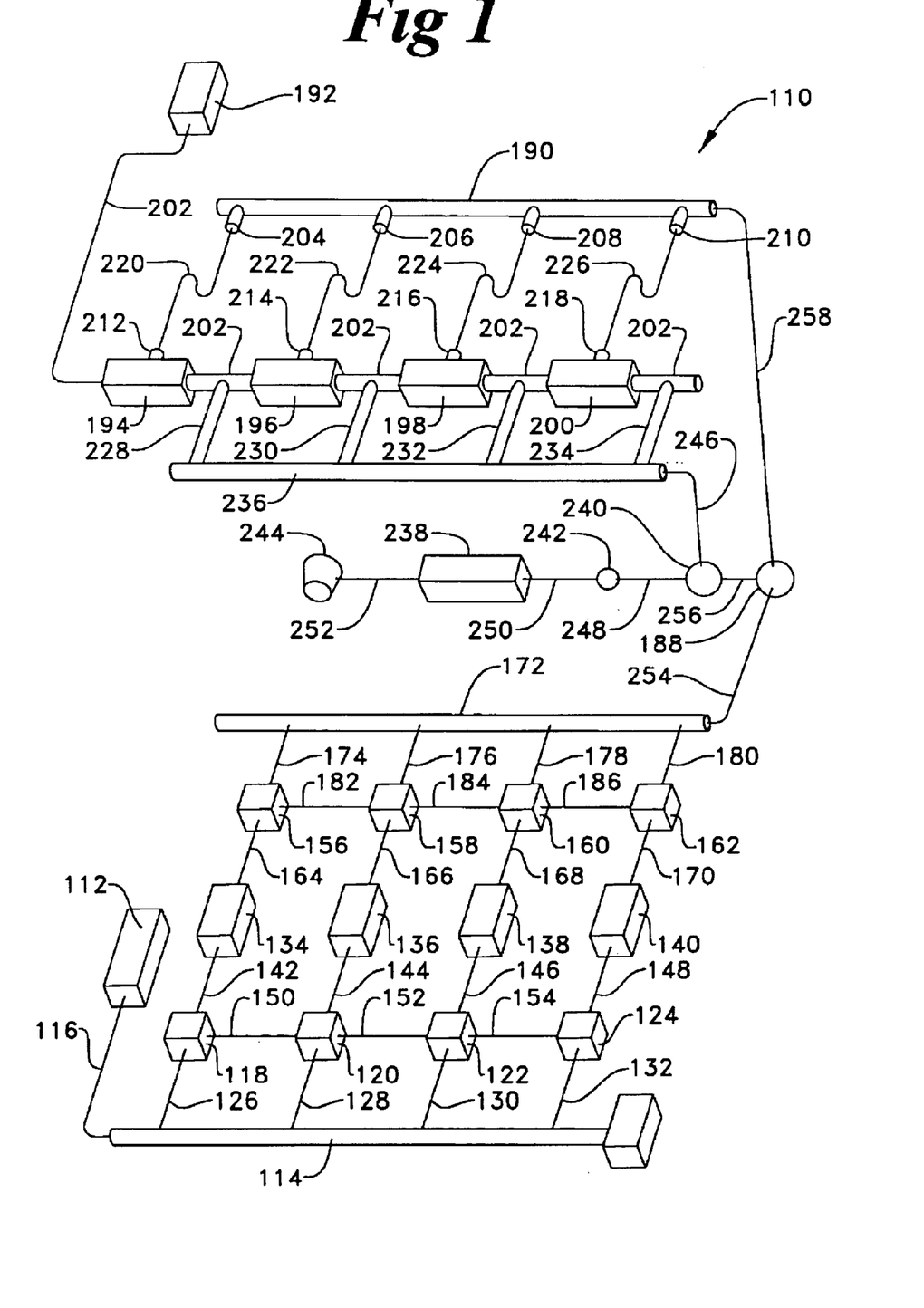
FIG. 1 is a schematic drawing of an embodiment of a multistage gas sampling and dilution control system.

Referring now to the drawings, and more particularly to FIG. 1, a first embodiment of a multistage gas sampling and dilution control system is generally indicated by the reference character 110. The system 110 is seen to have a dilution air source 112 which is provided for supplying dilution air to the system 110 in a manner, and for a purpose, which will be more fully appreciated hereinafter. More particularly, the dilution air source is fluidically connected to a first upstream manifold 114 by a fluid conduit 116. A plurality of calibration valves 118, 120, 122, 124 are arranged within a transverse array which is disposed fluidically downstream of the first upstream manifold 114 and are fluidically connected to the first upstream manifold 114 by a plurality of fluid conduits 126, 128, 130, 132 so as to receive dilution air from the first upstream manifold 114.

In a similar manner, a plurality of diluent mass flow controllers (DMFCs) 134, 136, 138, 140 are arranged within a transverse array which is disposed fluidically downstream of the calibration valves 118–124 and are respectively fluidically connected to the calibration valves 118–124 by a plurality of fluid conduits 142, 144, 146, 148. Adjacent ones of the calibration valves 118–124 are also fluidically interconnected to each other by a respective one of a plurality of additional fluid conduits 150, 152, 154. Calibration valves 118 and 124 have three-way valves respectively fluidically interconnecting fluid conduits 126, 142, 150 and 132, 148, 154, while calibration valves 120 and 122 have four-way valves respectively fluidically interconnecting fluid conduits 128, 144, 150, 152, and 130, 146, 152, 154.

Positioned fluidically downstream of the diluent mass flow controllers (DMFCs) 134–140, is a second transverse array of calibration valves 156, 158, 160, 162 which are similar to the first transverse array of calibration valves 118–124 and which are respectively fluidically connected to the downstream ends of the diluent mass flow controllers (DMFCs) 134–140 by a plurality of fluid conduits 164, 166, 168, 170. A second downstream manifold 172 is disposed fluidically downstream of the second transverse array of calibration valves 156–162. Each one of the calibration valves 156–162 is respectively fluidically connected to the second downstream manifold 172 by a fluid conduit 174, 176, 178, 180. Adjacent ones of the calibration valves 156–162 are fluidically interconnected to each other by one of a plurality of additional fluid conduits 182, 184, 186. Calibration valves 156 and 162 have three-way calibration valves respectively fluidically interconnecting fluid conduits 164, 174, 182 and 170, 180, 186, while calibration valves 158 and 160 has four-way calibration valves respectively fluidically inteconnecting fluid conduits 166, 176, 182, 184, and 168, 178, 184, 186.

Fluid flow from the second downstream manifold 172 passes through an upstream flow-control valve 188, and the downstream side of the upstream flow-control valve 188 is fluidically connected to a dilution air manifold 190 so as to provide dilution air to the dilution air manifold 190 as supplied by the dilution air source 112 after passing through the first upstream manifold 114, the first upstream transverse array of calibration valves 118–124, the diluent mass flow controllers (DMFCs) 134–140, the second downstream transverse array of calibration valves 156–162, and the second downstream manifold 172. Exhaust gases to be diluted and sampled for analytic are supplied into the system 110 by an internal combustion engine exhaust pipe 192, and a transverse array of exhaust gas diluters 194, 196, 198, 200 is disposed downstream of the dilution air manifold 190 whereby the gas diluters 194–200 are arranged in a serial manner.

Each one of the exhaust gas diluters 194–200 has a substantially identical structure. Each exhaust gas diluter 194–200 is simply shown schematically with FIG. 1. What is unique and new in connection with the gas sampling and dilution control system 110 of the present invention resides in the serial multistage arrangement of the exhaust gas diluters 194–200, and the fact that the internal combustion engine exhaust gas pipe 192 is not only fluidically connected to the first or upstream one of the exhaust gas diluters 194 by an exhaust gas conduit 202. The exhaust gas conduit 202 continues or extends through successive ones of the exhaust gas diluters 196–200 so as to successively or serially provide engine exhaust gases to the respective diluters 194–200. The serially arranged gas diluters 194–200 are thus disposed along the axial extent of the exhaust gas conduit 202.

In order to supply dilution air to each one of the exhaust gas diluters 194–200, the dilution air manifold 190 is provided with a plurality of pipe fittings 204, 206, 208, 210, each one of the exhaust gas diluters 194–200 is similarly provided with a pipe fitting 212, 214, 216, 218, and fluid conduits 220, 222, 224, 226 respectively interconnect the dilution air manifold pipe fittings 204–210 and the exhaust gas diluter pipe fittings 212–218. It is thus appreciated that the engine exhaust gases and dilution air mix together within each one of the exhaust gas diluters 194–200, and accordingly, various analytical sampling and measurement devices, components, or equipment, schematically illustrated at 228, 230, 232, 234, are advantageously operatively and fluidically connected to the exhaust gas conduit 202 at respective junctions downstream of each one of the exhaust gas diluters 194–200. In addition to the exhaust gas sampling, measuring, and analytical elements actually has the various devices, components, or equipment 228–234, as will be discussed more fully hereinafter. The devices, components, or equipment 228–234 also have fluid conduits which permit a portion of each one of the diluted exhaust gas streams flowing through exhaust gas conduit 202 to continue to flow through an exhaust gas or vacuum manifold 236.

The exhaust gas or vacuum manifold 236 is in turn fluidically connected to a total mass flow controller (TMFC) 238 through a downstream flow-control valve 240 and a filter 242. A vacuum pump 244 is fluidically connected to the downstream end of the total mass flow controller (TMFC) 238. More particularly, exhaust gas or vacuum manifold 236 is fluidically connected to the downstream flow-control valve 240 by a fluid conduit 246. Downstream flow-control valve 240 is fluidically connected to filter 242 by a fluid conduit 248, filter 242 is fluidically connected to the total mass flow controller (TMFC) 238 by a fluid conduit 250, and total mass flow controller (TMFC) 238 is fluidically connected to vacuum pump 244 by a fluid conduit 252. Upstream flow control valve 188 is also seen to be fluidically connected to the second downstream manifold 172 by a fluid conduit 254. Downstream flow control valve 240 is also fluidically connected to the upstream flow control valve 188 by a fluid conduit 256, and upstream flow control valve 188 is also fluidically connected to the dilution air manifold 190 by a fluid conduit 258. Each one of the flow control valves 188, 240 has a three-way valve wherein upstream flow control valve 188 fluidically interconnects fluid conduits 254–258, while downstream flow control valve 240 fluidically interconnects fluid conduits 246, 248, 256.

Figure 2:
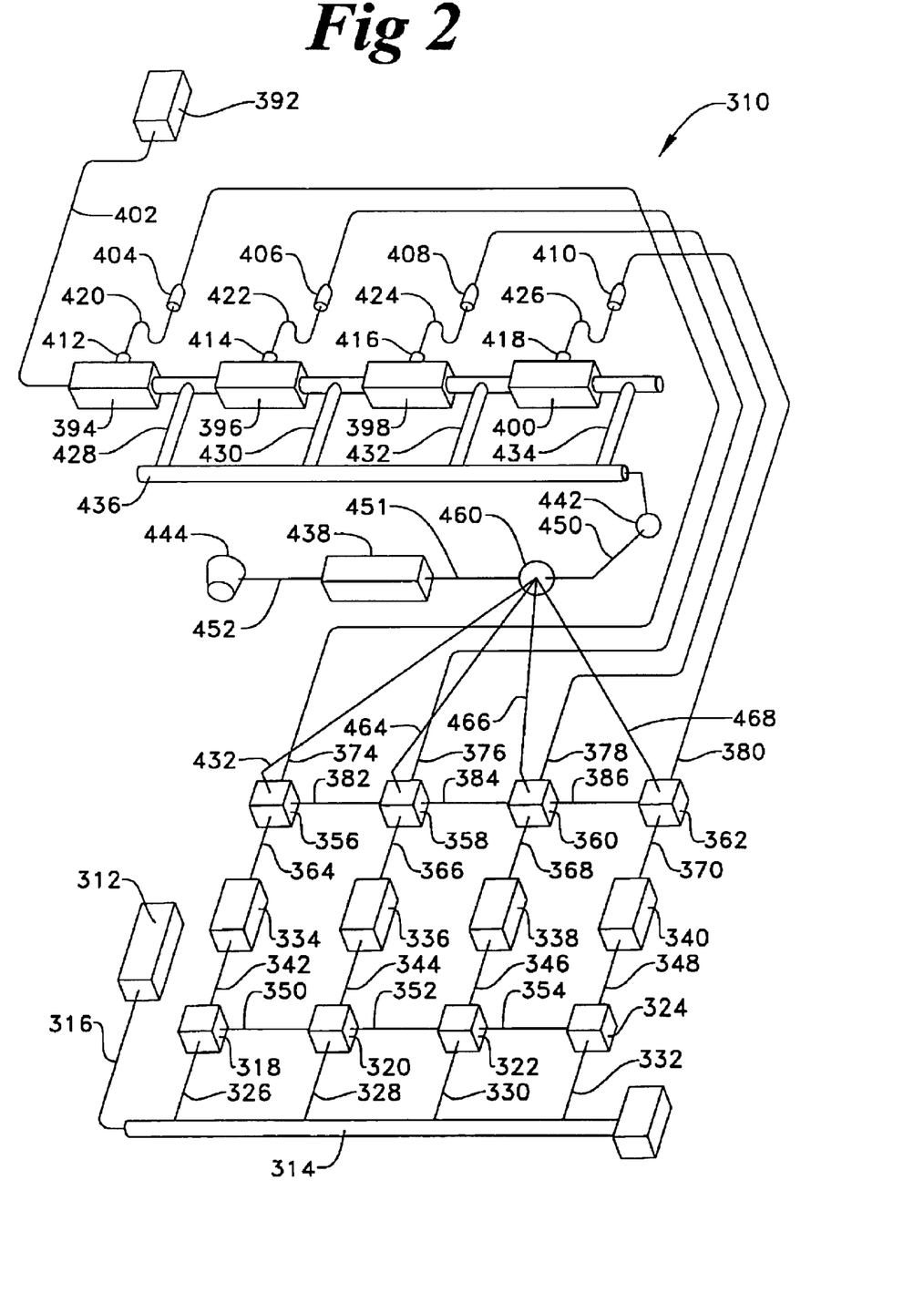
FIG. 2 is a schematic drawing of a second embodiment of a multistage gas sampling and dilution control system.

With reference to FIG. 2 of the drawings, another second embodiment of the multistage gas sampling and dilution control system is generally indicated by the reference character 310. The system 310 is seen to be essentially similar to the first embodiment of the present invention as disclosed and discussed in connection with FIG. 1, however, there are some differences between the two embodiment systems which will of course be discussed. In addition, it is noted that components or parts of the second embodiment system of the present invention as disclosed within FIG. 2 which correspond to similar components or parts of the first embodiment system of the present invention as disclosed within FIG. 1 are designated by similar reference characters except that the components or parts of the second embodiment system of the present invention are designated by reference numbers which are in the 300 and 400 series. Still further, in view of the employment of components or parts within the second embodiment system disclosed within FIG. 2 which are similar to components or parts within the first embodiment system disclosed within FIG. 1, a detailed discussion of all of such components or parts as disclosed within the second embodiment system of the present invention as disclosed within FIG. 2 will not be discussed as the disposition and function of such components or parts is already known.

One of the primary differences between the first and second embodiment systems disclosed within FIGS. 1 and 2 resides in the fact that in accordance with the second embodiment system 310, the second downstream manifold 172, the upstream flow-control valve 188, and the dilution air manifold 190 have been eliminated, and in lieu thereof, the second transverse array of calibration valves 356, 358, 360, 362 are respectively and directly connected to the pipe fittings 404, 406, 408, 410 by a plurality of fluid conduits 374, 376, 378, 380. In addition, downstream flow-control valve 240 has also been eliminated, and a six-way calibration control valve 460 has been fluidically interposed the filter 442 and the total mass flow controller (TMFC) 438 and is fluidically connected to the filter 442 by a fluid conduit 450 and is fluidically connected to the total mass flow controller (TMFC) 438 by a fluid conduit 451. Still further, the six-way calibration valve 460 is respectively fluidically connected to each one of the second transverse array of calibration valves 356–362 by a plurality of additional fluid conduits 462, 464, 466, 468. It will therefore be appreciated that these fluidic connections render the calibration valves 356 and 362 four-way calibration valves, while calibration valves 358 and 360 have five-way calibration valves in connection with the additional fluid conduits 382, 384, 386 fluidically interconnecting adjacent ones or pairs of the calibration valves 356–362.

Figure 3:
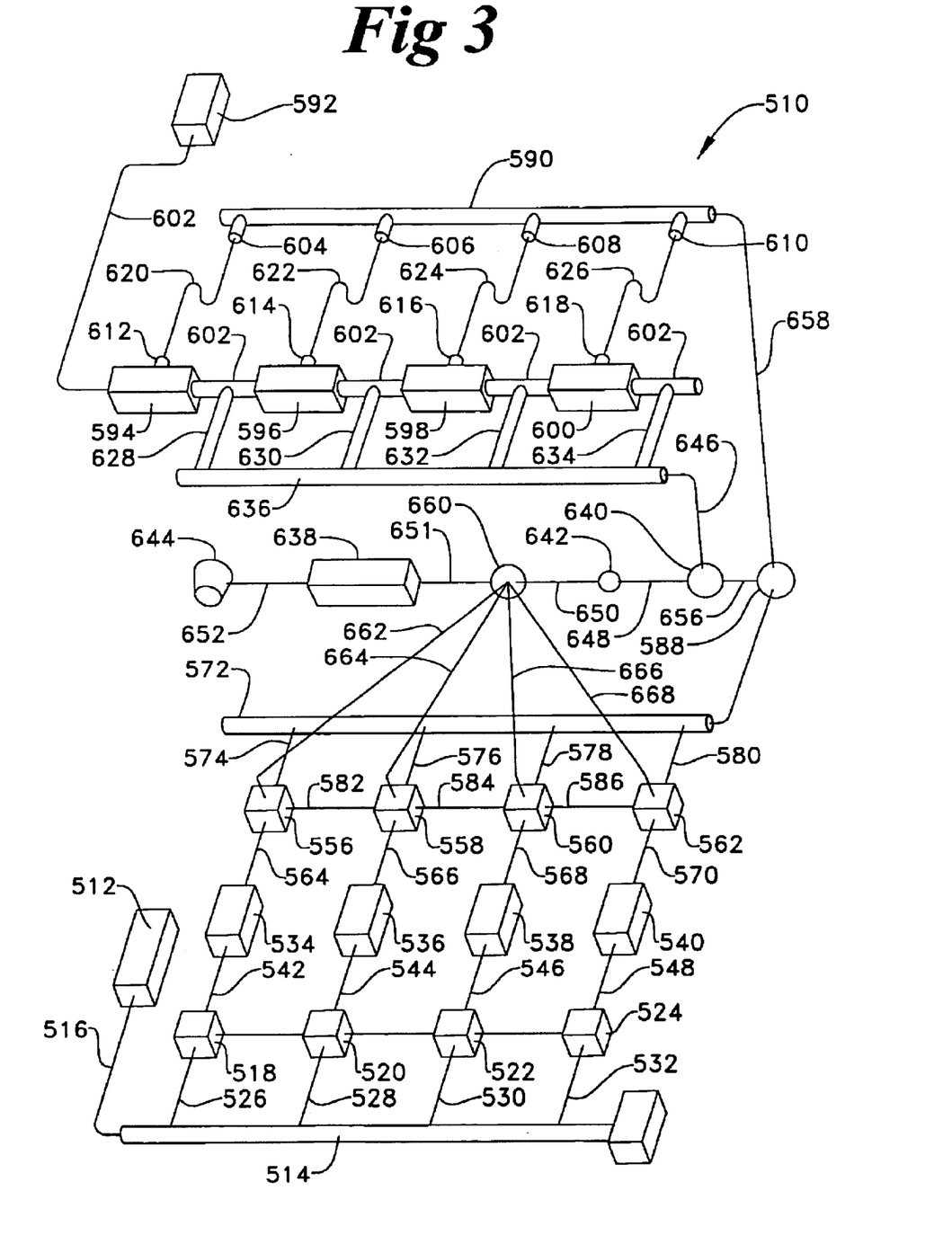
FIG. 3 is a schematic drawing of a third embodiment of a multistage gas sampling and dilution control system.

With reference to FIG. 3 of the drawings, another or third embodiment of a multistage gas sampling and dilution control system is generally indicated by the reference character 510. The system 510 is seen to be essentially similar to the first and second embodiments of the present invention as disclosed and discussed in connection with FIGS. 1 and 2, however, there are some differences between the embodiment systems which will of course be discussed. In addition, it is noted that components or parts of the third embodiment system of the present invention as disclosed within FIG. 3 which correspond to similar components or parts of the first and second embodiment systems of the present invention as disclosed within FIGS. 1 and 2 are designated by similar reference characters except that the components or parts of the third embodiment system of the present invention are designated by reference numbers which are in the 500 and 600 series. Still further, in view of the employment of components or parts within the third embodiment system disclosed within FIG. 3 which are similar to components or parts within the first and second embodiment systems disclosed within FIGS. 1 and 2, a detailed discussion of all of such components or parts are disclosed within the third embodiment system of the present invention as disclosed within FIG. 3 will not be discussed as the disposition and function of such components or parts is already known.

The third embodiment of the multistage gas sampling and dilution control system 510 has in effect a hybrid or composite of the first and second embodiment systems 110 and 310 as disclosed within FIGS. 1 and 2. There is provided a second downstream manifold 572, a dilution air manifold 590, a upstream flow-control valve 588, and a downstream flow-control valve 640. In a similar manner, as was the case of the second embodiment system as disclosed within FIG. 2, a six-way calibration valve 660 is also provided along with a plurality of fluid conduits, 662, 664, 666, 668 which respectively fluidically interconnect the second array of calibration valves 556, 558, 560, 562 to the six-way calibration valve 660.

Figure 4:
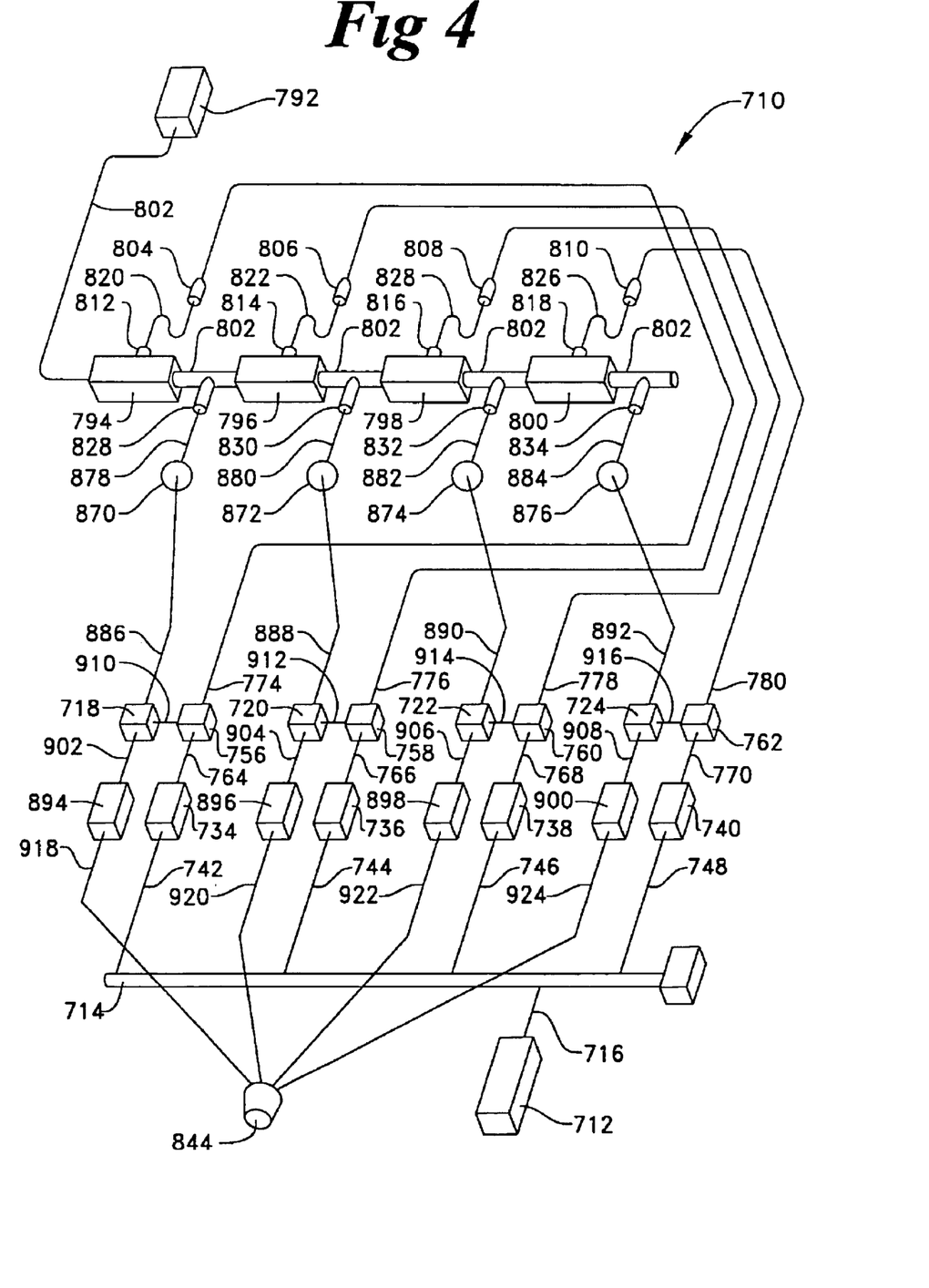
FIG. 4 is a schematic drawing of a fourth embodiment of a multistage gas sampling and dilution control system.

With reference to FIG. 4, another or fourth embodiment of a multistage gas sampling and dilution control system is disclosed and is generally indicated by the reference character 710. The system 710 is seen to be operatively similar to the first, second, and third embodiments of the present invention as disclosed and discussed in connection with FIGS. 1–3, however, there are some differences between the embodiment systems which will of course be discussed. In addition, it is noted that components or parts of the fourth embodiment system of the present invention disclosed within FIG. 4 which correspond to similar components or parts of the first, second and third embodiment systems of the present invention as disclosed within FIGS. 1–3 are designated by similar reference characters except that the components or parts of the fourth embodiment system of the present invention are designated by reference numbers which are in the 700, 800, and 900 series. Still further, in view of the employment of components or parts within the fourth embodiment system disclosed within FIG. 4 which are similar to components or parts within the first, second, and third embodiment systems disclosed within FIGS. 1–3, a detailed discussion of all of such components or parts as disclosed within the fourth embodiment system of the present invention as disclosed within FIG. 4 will not be discussed as the disposition and function of such components or parts is already known.

It is seen that the fourth embodiment system 710 of the present invention has in effect what may be considered a more simplified embodiment or version of the present invention as compared to the first, second, and third embodiment systems 110, 310 and 510 as disclosed within FIGS. 1–3 in that both the dilution air manifold and the vacuum manifold have been eliminated and in a manner similar to that of the second embodiment system disclosed within FIG. 2. Each one of the downstream transverse array of a plurality of calibration valves 756, 758, 760, 762 is directly fluidically connected to their respective pipe fittings 804, 806, 808, 810 through a plurality of fluid conduits 774, 776, 778, 780. In addition, the upstream transverse array of calibration valves 718, 720, 722, 724 has in effect been relocated such that each one of the upstream calibration valves 718–724 is disposed in a paired relationship with a corresponding one of the downstream calibration valves 756–762.

Furthermore, in view of the aforenoted elimination of the vacuum manifold, each one of the fluid conduits has the devices, components, or equipment 828, 830, 832, 834 is fluidically connected to a respective one of the relocated upstream transverse array of calibration valves 718–724 through a suitable filter element 870, 872, 874, 876. Fluid conduits 878, 880, 882, 884 respectively fluidically interconnect the devices, components, or equipment 828–834 and the filter elements 870–876, while fluid conduits 886, 888, 890, 892 respectively fluidically interconnect the filter elements 870–876 to the relocated upstream transverse array of calibration valves 718–724.

Continuing further, in view of the fact that the upstream transverse array of calibration valves 718–724 have now been relocated, the diluent mass flow controllers (DMFCs) 734, 736, 738, 740 are directly fluidically connected to the upstream manifold 714 through a plurality fluid conduits 742, 744, 746, 748. What is also uniquely new and novel in connection with this fourth embodiment system of the present invention is the provision of individual total mass flow controllers (TMFCS) 894, 896, 898, 900 which are respectively fluidically connected to the relocated upstream transverse array of calibration valves 718–724 through a plurality of fluid conduits 902, 904, 906, 908. Still further, the relocated upstream transverse array of calibration valves 718–724 are respectively fluidically connected to their paired downstream transverse array of calibration valves 756–762 through a plurality of conduits 910–912, 914, 916. Each one of the relocated upstream calibration valves 718–724, as well as each one of the downstream calibration valves 756–762 has a three-way valve. Lastly, it is also seen that the total mass flow controller (TMFCs) are also respectively fluidically connected to the vacuum pump 844 by a plurality of fluid conduits 918, 920, 922, 924.

Industrial Applicability

In operation the present multistage gas sampling and dilution control system 110 is disclosed in FIG. 1, the various first upstream and second downstream transverse arrays of calibration valves 118–124 and 156–162 can be suitably or appropriately controlled in such manner that the various fluid flows through any one or a group of the diluent mass flow controllers (DMFCs) 134–140 can be calibrated in connection with each other, other groups of such flow controllers, and also with respect to the fluid flow flowing through the total mass flow controller (TMFC) 238. Opening or closing, the various calibration valves 118–124 and/or 156–162, various different flow control loops are established which permit the mass flow control monitoring and calibration of the various diluent mass flow controllers (DMFCs) 134–140 with respect to each other and with respect to the total mass flow controller (TMFC) 238.

As one example of such flow control and calibration, valves 118 and 156 are controlled so as to permit fluid flow through diluent mass flow controller (DMFC) 134, and in addition, valve 156 is controlled so as to block flow through manifold 172 and permit flow into conduit 182. Valves 158 and 120 are also controlled so as to permit fluid flow through diluent mass flow controller (DMFC) 136 and conduit 150 so as to in effect establish a closed loop fluid flow circuit through the diluent mass flow controllers (DMFCs) 134, 136 whereby the same can be calibrated with respect to each other. Valves 122 and 124 are also controlled so as to prevent fluid flow through diluent mass flow controllers (DMFCS) 138 and 140 at this time, although, of course, similar calibration operations or techniques can of course be performed in connection with such diluent mass flow controllers (DMFC) 138, 140, or still alternatively, with respect to other pairs of the diluent mass flow controllers (DMFCs) 134–140.

In addition, flow through only a single one of the diluent mass flow controllers (TMFC) 238 can be performed or controlled such that the flow through such isolated diluent mass flow controller (DMFC) can be calibrated with respect to the total mass flow controller (TMFC) 238 as a result of the additional operation of, for example, flow control valves 188 and 240. Still further, as can be appreciated from the second and third embodiments of FIGS. 2 and 3, by the provision of the six-way valves 460, 660, and the fluidic connections of such valves 460, 660 to the downstream transverse array of calibration valves 356–362 and 556–562, the calibration of the diluent mass flow controllers (DMFCs) 334–340 and 534–540 with respect to the total mass flow controllers (TMFCs) 438 and 638 can be achieved more simply with the embodiment system of FIG. 2, without the need for requiring the fluid flows to flow through the manifold 172 and the valves 188 and 240, or in accordance with the embodiment system of FIG. 3, without the need for requiring the fluid flows to flow through the valves 588 and 640.

In a similar manner, simplified calibration of the diluent mass flow controllers (DMFCs) 734–740 with respect to their corresponding total mass flow controllers (TMFCs) 894–900 can also be appreciated from the fourth embodiment system of FIG. 4 as achieved through appropriate control of the downstream transverse array of calibration valves 756–762 as well as the appropriate control of the relocated upstream array of calibration valves 718–724. More particularly, for example, in connection with the calibration of diluent mass flow controller (DMFC) 734 with respect to its corresponding total mass flow controller (TMFC) 894, appropriate control of the downstream and upstream calibration valves 756 and 718 effectively serve to define a closed fluidic loop having air source 712, manifold 714, conduit 742, diluent mass flow controller (DMFC) 734, conduit 764, calibration valve 756, conduit 910, calibration valve 718, conduit 902, total mass flow controller (TMFC) 894, conduit 918, and pump 844. Each one of the mass flow controllers per se is conventional and may be a Model 860 which can be obtained from Sierra Instruments, Monterrey, Calif.

With reference again being made to the first embodiment system of the present invention as disclosed within FIG. 1, although the same discussion is of course applicable to any one of the other embodiment systems of FIGS. 2–4, it is critical to appreciate that the present invention, environmental or atmospheric pollution conditions as they exist in the real world can effectively be replicated and therefore suitably monitored, analyzed, and the like. More particularly, with reference being made to the embodiment system of FIG. 1, it is seen that exhaust gases from an internal combustion engine, not shown, are supplied or delivered into the system 110 by the engine exhaust pipe 192 and the connecting exhaust gas conduit 202, and that the latter conduit 202 extends axially through each one of the exhaust gas diluters 194–200 which are of course disposed in their related serial array. Dilution air is supplied into each one of the exhaust gas diluters 194–200 from dilution air manifold 190 by the pipe fittings 204–210, 212–218, and connecting conduits 220–226. Consequently, the exhaust gas flow flowing through the conduit 202 is serially and continuously diluted in a controlled manner as predetermined by the various parameters or characteristics of the particular exhaust gas diluters 194–200 as the exhaust gases are serially conducted and serially travel through the diluters 194–200. Therefore, each diluter 194–200, and the degree to which the exhaust gases are diluted by the dilution air flowing through the particular diluter 194–200, serves to simulate or replicate a real world pollution condition to be monitored and analyzed.

For example, the amount or degree to which the exhaust gases from the exhaust pipe 192 are initially diluted within the first or upstream diluter 194 may be correlated with the environmental air-exhaust gas stream or conditions which are present or which exist within the atmosphere at a position relative to, for example, a tractor-trailer vehicle which corresponds to an axial position, as taken along the length of the tractor-trailer vehicle, which may be located between the vehicle tractor cab and the vehicle trailer. In a similar manner, the amount or degree to which the exhaust gases from the exhaust pipe 192 are further diluted within the second diluter 196 may be correlated with the environmental air-exhaust gas stream or conditions which are present, or which exist, within the atmosphere at a position, relative to the tractor-trailer vehicle, which corresponds to an axial position, as taken along the length of the tractor-trailer vehicle, which may be located along the vehicle trailer.

The amount or degree to which the exhaust gases from the exhaust pipe 192 are further diluted within the third diluter 198 may be correlated with the environmental air-exhaust gas stream or conditions which are present, or which exist, within the atmosphere at a position, relative to the tractor-trailer vehicle, which corresponds to an axial position, as taken along the length of the tractor-trailer vehicle, which may be located at the end of the vehicle trailer. Lastly, the amount or degree to which the exhaust gases from the exhaust pipe 192 are further diluted within the fourth diluter 200 may be correlated with the environmental air-exhaust gas stream or conditions which are present, or which exist, within the atmosphere at a position, relative to the tractor-trailer vehicle, which corresponds to an axial position, as taken along the length of the tractor-trailer vehicle, which may be located, for example, a predetermined distance aft of the vehicle trailer. In this manner, real-life atmospheric conditions can be monitored and analyzed.

In particular, the various devices, components, or equipment which is schematically illustrated at 228–234 may have various types of particle size measurement or classification units attached to the diluters in serial communication. These measurements and/or classifications apparatus are typically used with particle counters. It should be understood that not all measurement/classification devices employ separate particle counters, as some are integral. It should also be recognized that the diluters can be used for particle count determination in the absence of particle sizing and/or segmentation devices. Particle sizing considers diameter, surface area and particle volume, the invention described herein is intended for use with any of these systems.

The most common technology for particle size quantification and number count determination is the scanning mobility particle sizer (SMPS) in tandem with a condensation particle counter (CPC). Such particle sizer instrumentation is conventionally available as Model Number 3934 from Thermal Sciences, Inc. of St. Paul, Minn., and the particle counter instrumentation is also available from such company as Model Number 3025. With such instrumentation, the size and number of pollutant particles can be readily determined within the various flow streams as noted hereinbefore. The various operating or dilution parameters characteristic of the diluters 194–200 may be predeterminedly varied for example, the length dimensions of the diluters, the flow rates of the dilution air through the diluters, the dilution air ratio, that is, the amount of dilution air relative to the amount of the exhaust gas, and the like.

Serially located diluters are arranged for providing dilution into an engine exhaust stream so as to effectively replicate real-world highway atmospheric conditions to which the populace is subjected. In conjunction with the diluter components, various particle sizer and particle counter instrumentation are employed so as to determine the pollutant characteristics of the exhaust streams at the various positions at which the diluters are effectively disposed which simulate the different axial atmospheric positions relative to, for example, a tractor-trailer vehicle exhausting exhaust gases into the atmosphere.

Obviously, many variations and modifications of the present invention are possible in light of the above teachings. It is therefore to be understood that within the scope of the appended claims, the present invention may be practiced otherwise than as specifically described herein.

Other aspects, objects and advantage of this invention can be obtained from a study of the drawings, the disclosure and the appended claims.

What is claimed is:

1. A gas sampling system, comprising:
   a plurality of diluters arranged in a serial array along an axial extent;
   a source of dilution air fluidically connected to each one of said plurality of serially arranged diluters so as to supply dilution air into each one of said plurality of serially arranged diluters such that said dilution air is supplied into a gas stream present within each one of said plurality of serially arranged diluters so as to progressively dilute said gas stream as said gas stream flows through said plurality of serially arranged diluters;
   sampling apparatus fluidically connected to each one of said plurality of serially arranged diluters for obtaining and analyzing a sample of said diluted gas stream present within each one of said plurality of serially arranged diluters; and
   a plurality of diluent mass flow controllers (DMFCs) disposed fluidically upstream of said plurality of serially arranged diluters for monitoring the mass flow of dilution air being supplied to said plurality of serially arranged diluters, and at least one total mass flow controller (TMFC) disposed fluidically downstream of said plurality of serially arranged diluters for monitoring the mass flow of diluted air stream flowing through said plurality of serially arranged diluters.

2. The system as set forth in claim 1 wherein said at least one total mass flow controller (TMFC) includes a plurality of total mass flow controllers (TMFCs) fluidically connected respectively to each one of said plurality of serially arranged diluters.

3. The system as set forth in claim 2 wherein each one of said plurality of total mass flow controllers (TMFCs) is operatively associated with a respective one of said diluent mass flow controllers (DMFCs) such that said diluent mass flow controllers (DMFCs) and said total mass flow controllers (TMFCs) are arranged in operative pairs.

4. A The system as set forth in claim 3 including a calibration valves fluidically connected to each one of said diluent mass flow controllers (DMFCs) and fluidically connected to each one of said total mass flow controllers (TMFCs) so as to permit calibration of each one of said diluent mass flow controllers (DMFCs) with respect to its paired total mass flow controller (TMFC).

5. The system as set forth in claim 1 wherein each one of said plurality of diluent mass flow controllers (DMFCs) is fluidically connected directly to a respective one of said plurality of serially arranged diluters.

6. The system as set forth in claim 1 wherein an air dilution manifold is disposed fluidically upstream of said plurality of serially arranged diluters, and said plurality of diluent mass flow controllers are fluidically connected to said air dilution manifold so as to supply diluent air to said plurality of serially arranged diluters through said air dilution manifold.

7. The system as set forth in claim 1 including a plurality of calibration valves fluidically connected to each one of said plurality of diluent mass flow controllers (DMFCS) so as to permit calibration of each one of said diluent mass flow controllers (DMFCS) with respect each other.

8. The system as set forth in claim 1 including a plurality of calibration valves fluidically connected to each one of said plurality of diluent mass flow controllers (DMFCs) so as to permit calibration of each one of said plurality of diluent mass flow controllers (DMFCs) with respect to each other and with respect to said at least one total mass flow controller (TMFC).

9. The system as set forth in claim 8 including a calibration control valve fluidically interposed said plurality of calibration valves and said at least one total mass flow controller (TMFC) for selectively permitting calibration of a particular one of said plurality of diluent mass flow controllers (DMFCs) with respect to said at least one total mass flow controller (TMFC).

10. An exhaust gas sampling system for use in connection with the sampling of internal combustion engine exhaust gas streams, comprising:
    a plurality of diluters arranged in a serial array along an axial extent;
    a source of engine exhaust gas fluidically connected to said plurality of serially arranged diluters so as to supply an engine exhaust gas stream into each one of said plurality of serially arranged diluters in a serial manner;
    a source of dilution air fluidically connected to each one of said plurality of serially arranged diluters so as to supply dilution air into each one of said plurality of serially arranged diluters such that said dilution air is supplied into said engine exhaust gas stream present within each one of said plurality of serially arranged diluters so as to progressively dilute said engine exhaust gas stream as said engine exhaust gas stream flows through said plurality of serially arranged diluters and thereby replicate engine exhaust gas stream pollutant atmospheric conditions;
    a sampling apparatus fluidically connected to each one of said plurality of serially arranged diluters for obtaining and analyzing a sample of said diluted engine exhaust gas stream present within each one of said plurality of serially arranged diluters; and
    a plurality of diluent mass flow controllers (DNFCs) disposed fluidically upstream of said plurality of serially arranged diluters for monitoring the mass flow of dilution air being supplied to said plurality of serially arranged diluters, and at least one total mass flow controller (TMFC) disposed fluidically downstream of said plurality of serially arranged diluters for monitoring the mass flow of the diluted air stream flowing through said plurality of serially arranged diluters.

11. The system as set forth in claim 10 wherein said at least one total mass flow controller (TMFC) includes a plurality of total mass flow controllers (TMFCs) fluidically connected respectively to each one of said plurality of serially arranged diluters.

12. The system as set forth in claim 11 wherein each one of said plurality of total mass flow controllers (TMFCs) is operatively associated with a respective one of said diluent mass flow controllers (DMFCs) such that said diluent mass flow controllers (TMFCs) are arranged in operative pairs.

13. The system as set forth in claim 12 including a calibration valves fluidically connected to each one of said diluent mass flow controllers (DMFCs) and fluidically connected to each one of said total mass flow controllers (TMFCs) so as to permit calibration of each one of said diluent mass flow controllers (DMFCs) with respect to its paired total mass flow controller (TMFC).

14. The system as set forth in claim 10 wherein each one of said plurality of diluent mass flow controllers (DMFCs) is fluidically connected directly to a respective one of said plurality of serially arranged diluters.

15. The system as set forth in claim 10 including an air dilution manifold disposed fluidically upstream of said plurality of serially arranged diluters, and said plurality of diluent mass flow controllers are fluidically connected to said air dilution manifold so as to supply diluent air to said plurality of serially arranged diluters through said air dilution manifold.

16. The system as set forth in claim 10 including a plurality of calibration valves fluidically connected to each one of said plurality of diluent mass flow controllers (DMFCs) so as to permit calibration of each one of said diluent mass flow controllers (DMFCs) with respect to each other.

17. The system as set forth in claim 10 including a plurality of calibration valves fluidically connected to each one of said plurality of diluent mass flow controllers (DMFCs) so as to permit calibration of each one of said plurality of diluent mass flow controllers (DMFCs) with respect to each other and with respect to said at least one total mass flow controller (TMFC).

18. The system as set forth in claim 17 including a calibration control valve fluidically interposed said plurality of calibration valves and said at least one total mass flow controller (TMFC) for selectively permitting calibration of a particular one of said plurality of diluent mass flow controllers (DMFCs) with respect to said at least one total mass flow controller (TMFC).

* * * * *